(12) United States Patent
Beaudoin et al.

(10) Patent No.: US 6,800,284 B2
(45) Date of Patent: Oct. 5, 2004

(54) ATP-DIPHOSPHOHYDROLASES, PROCESS OF PURIFICATION THEREOF AND PROCESS OF PRODUCING THEREOF BY RECOMBINANT TECHNOLOGY

(75) Inventors: Adrien R. Beaudoin, Rock Forest (CA); Jean Sevigny, Brookline, MA (US)

(73) Assignee: Universite de Sherbrooke, Sherbrooke (CA)

( * ) Notice: Subject to any disclaimer, the term of this patent is extended or adjusted under 35 U.S.C. 154(b) by 0 days.

(21) Appl. No.: 09/781,796

(22) Filed: Feb. 12, 2001

(65) Prior Publication Data

US 2003/0040094 A1 Feb. 27, 2003

Related U.S. Application Data

(62) Division of application No. 08/930,921, filed on Jan. 2, 1998, now Pat. No. 6,287,837, which is a continuation of application No. 08/777,859, filed on Dec. 31, 1996, now Pat. No. 5,798,241, which is a continuation of application No. 08/419,204, filed on Apr. 10, 1995, now abandoned.

(51) Int. Cl.$^7$ .................. A61K 38/46; C12N 11/00; C12N 9/76; C12N 9/22; C12N 9/96
(52) U.S. Cl. .............. 424/94.6; 435/174; 435/177; 435/180; 435/195
(58) Field of Search ................ 435/196, 174, 435/177, 180, 195; 424/94.6

(56) References Cited

U.S. PATENT DOCUMENTS 5,798,241 A   8/1998   Beaudoin et al.

FOREIGN PATENT DOCUMENTS

| WO | WO94/02015 | 3/1994 |
| WO | WO96/32471 | * 10/1996 |

OTHER PUBLICATIONS

Yagi et al, 1989, Eur. J. Biochem. 180 (3): 509–513.
Cote et al., 1991, Biochem. Biophys. Acta 1078: 187–191.
Maliszewski et al., 1994, The Journal of Immunology 153: 3574–3583.
Lebel et al., 1980, Journal biol. Chem., 255: 1227–1233.
Laliberte et al., 1982, J. Biol. Chem., 255: 1227–1233.
Moodie et al., 1991, Eur. J. Biochem., 202:1209–1215.
Miura et al., 1987, Thromb. Res., 46: 685–696.
Cote et al., 1992, Biochemica and Biophysica Acta 1139: 133–142.
Baykov et al., 1988, Anal. Biochem. 171:266–270.
Bradford M.M., 1976, Anal. Biochem. 72: 248–254.
Christoforidis et al., Eur. J. Biochem. 234:66–74.
Hirota et al., 1987, Thrombosis Res., 45: 201–209.
Laemmli U.K., 1970, Nature 227: 680–685.
Patel et al., 1969, BBA 178:626–629.
Rigbi et al., 1987, Comp. Biochem. Physiol. 87B: 567–573.
Yagi et al., 1992, Chem. Pharm. Bull. 40: 2143–2146.

* cited by examiner

Primary Examiner—Herbert J. Lilling
(74) Attorney, Agent, or Firm—Quarles & Brady LLP

(57) ABSTRACT

The present invention relates to two ATP diphosphohydrolases (ATPDase enzymes) isolated from bovine aorta and pig pancreas, which enzymes have a molecular weight for their catalytic unit of about 78 and 54 Kilodaltons, respectively. A first process for obtaining a highly purified ATPDase is also an object of the present invention. This process has been successfully applied to the purification of both the pancreatic and the aorta enzymes and is deemed to work in the purification of any ATPDase. For both sources of enzymes, the process allows the specific activity of the enzyme to be increased by at least 10,000 fold when compared to the activity retrieved in the crude cell homogenates. The novel process involves an ion exchange chromatography step, a separation on an affinity column, followed by an electrophoresis under non-denaturing conditions. The two enzymes purified by this process (aortic and pancreatic) are glycosylated and, when deglycosylated, have molecular weights shifted to about 56 and 35 Kdaltons, respectively. Partial amino acid sequences have been obtained for each enzyme. The partial sequences appear highly homologous with a human lymphoid cell activation antigen named CD39. An antibody directed against the porcine pancreatic enzyme cross-reacts with a protein present in endothelial cell lines and in bovine aorta (78 KDa). The high degree of homology of the pancreatic and aortic enzymes with CD39 and their cross-reactivity are indications that both enzymes are related. The pancreatic enzyme completely lacks the first 200 amino acids of CD39, which means the ATPDase activity is comprised between residues 200 and 510 of CD39. Since this is the first time that a sequence is assigned to ATPDases, a second new process for producing ATPDases by recombinant technology can also be used. Therefore a second new process for producing an ATPDase using the CD39-encoding nucleic acid or part or variant thereof is also described.

23 Claims, 5 Drawing Sheets

Western Blot

ATP-DIPHOSPHOHYDROLASES, PROCESS OF PURIFICATION THEREOF AND PROCESS OF PRODUCING THEREOF BY RECOMBINANT TECHNOLOGY

CROSS-REFERENCE TO RELATED APPLICATIONS

This application is a divisional application of U.S. application Ser. No. 08/930,921, filed on Jan. 2, 1998, now U.S. Pat. No. 6,287,837, which is a continuation application of U.S. application Ser. No. 08/777,859, filed on Dec. 31, 1996, now U.S. Pat. No. 5,798,241, which is a continuation application of U.S. application Ser. No. 08/419,204, filed on Apr. 10, 1995, now abandoned.

FIELD OF THE INVENTION

The present invention relates to a process of purification to homogeneity of ATP-diphosphohydrolases involved in numerous nucleotide and nucleoside receptor-mediated physiological functions, namely platelet aggregation, vascular tone, secretory, inflammatory and excretory functions and neurotransmission. These enzymes, which have been particularly obtained from bovine aorta and pig pancreas have been purified and their catalytic unit identified. The partial amino acid sequences of each ATPDase show a high degree of homology with a lymphoid cell activation system named CD39.

BACKGROUND OF THE INVENTION

ATP-diphosphohydrolases (ATPDases) or apyrases (EC 3.6.1.5) have been found in plants, invertebrates and vertebrates. The enzyme catalyses the sequential hydrolysis of the ν- and β-phosphate residues of triphospho- and diphosphonucleosides. These enzymes are generally activated in the presence of divalent cations $Ca^{+2}$ or $Mg^{+2}$ and inhibited by sodium azide. In plants, the enzymes are found in the cytoplasm, in soluble or membrane-associated forms, and are generally more active at acid pH. Their precise function is not known, but there is some evidence that they are involved in the synthesis of carbohydrates. In invertebrates, the enzymes are more active at neutral or alkaline pH. Found mainly in saliva and in salivary glands of hematophagous insects, an antihemostatic role has been demonstrated. In vertebrates, a limited number of studies have already defined a diversity of ATPDases. The catalytic site of these enzymes is generally exposed to extracytoplasmic spaces (ectoenzymes). By their location and kinetic properties, these different types of ATPDases could influence the main systems of the organism, namely vascular and nervous systems. Their specific role in these systems is determined by the presence of purine and pyrimidine receptors which react with triphosphonucleosides and their derivatives at the surface of numerous cell types.

Presence of both ectoATPase and ectoADPase activities in the vascular system has been known for many years, and up until the work of Yagi et al. (1989), they were attributed to two distinct enzymes. The latter purified these activities and showed that in bovine aorta, a single enzyme was responsible for the sequential hydrolysis of ATP and ADP. A mammalian ATPDase had been first described in the pancreas (Lebel et al., 1980) and was further reported in several other tissues. Yagi et al. (1989) proposed that the enzyme from aorta was similar to the previously reported mammalian ATPDase from pancreas and that it was associated with the intima of bovine aorta. Purification to homogeneity was demonstrated by SDS-polyacrylamide gel electrophoresis (PAGE) and silver staining. The apparent molecular weight of the pure enzyme was estimated at 110 KDa. The existence of the ATPDase in the bovine aorta was corroborated by Côté et al. (1991) who, by showing that identical heat and irradiation-inactivation curves with ATP and ADP as substrates, assigned to the same catalytic site the ATPase and ADPase activities. A comparison of the biochemical properties led Côté et al. supra to propose that the bovine aorta enzyme was different from the pancreas ATPDase. Indeed, the enzymes have different native molecular weights, optimum pH and sensitivities to inhibitors. They proposed to identify pancreas enzyme as type I and the aorta enzyme as type II. In the bovine aorta, the enzyme was found to be associated with smooth muscle cells and endothelial cells and could inhibit ADP-induced platelet aggregation. Côté et al. (1991) further showed that concurrent addition of ATPDase and ATP to platelet-rich plasma resulted in an immediate dose-dependent platelet aggregation caused by the accumulation of ADP, followed by a slow desaggregation attributable to its hydrolysis to AMP. In the absence of ATPDase, ATP did not induce any aggregation while ADP initiate an irreversible aggregation which extent is limited by the ADPase activity of the enzyme. ATPDase also attenuated the aggregation elicited by thrombin and collagen but not by PAF (Platelet Activating Factor), the first two agonists having an effect mediated by platelet ADP release. It was therefore suggested that ATPDase had a dual role in regulating platelet activation. By converting ATP released from damaged vessel cells into ADP, the enzyme induced platelet aggregation at the sites of vascular injury. By converting ADP released from aggregated platelets and/or from hemolyzed red blood cells to AMP, the ATPDase could inhibit or reverse platelet activation, and consequently limit the growth of platelet thrombus at the site of injury. In their attempt to further characterize the aorta ATPDase, the present inventors have developed a new process for producing highly purified ATPDases. They have established a procedure by which its specific activity can be increased over and above the activity of a crude cell preparation by more than 10000-fold. They also discover that the purified enzyme (the catalytic unit) had a molecular weight different from the one previously reported for the native form of the enzyme (190 KD by using the irradiation technique), suggesting that the enzyme may exist in a multimeric form in its native state. Partial amino acid sequences of both bovine aorta and porcine pancreatic ATPases have been obtained.

In a completely different field, Maliszenski et al. (1994) have published the sequence of a human lymphoid cell activation antigen designated CD39. Another group (Christoforidis et al. 1995) described the purification of a human placenta ATPDase of a molecular weight of 82 KDa. Its partial amino acid sequence shows a high degree of homology with CD39.

When the above mentioned partial amino acid sequences were entered in GenBank for verifying the presence of any homologous sequence, complete homology was surprisingly found for some of these fragments with the CD39 gene product. The complete sequences of the ATPDases remain to be obtained. Assuming that CD39 is an up to date unknown ATPDase, a process for producing ATPDases by recombinant technology is now possible, and CD39 can now be used to reduce platelet aggregation and thrombogenicity.

STATEMENT OF THE INVENTION

It is an object of the present invention to provide two ATPDases isolated from bovine aorta and porcine pancreas, which enzymes have a molecular weight for their catalytic unit of about 78 and 54 Kilodaltons, respectively. A novel process for obtaining a highly purified ATPDase is also an object of the present invention. This process has been successfully applied to the purification of both the pancreatic and the aorta enzymes and is deemed to work in the purification of any ATPDase. For both sources of enzymes, the process allows the specific activity of the enzyme to be increased by at least 300 fold when compared to the activity retrieved in the microsomial fraction of these cells as previously reported for an aortic and pancreatic proteins of a native molecular weight of about 190 and 130 KDa, respectively.

The two ATPDases purified to homogeneity were partially sequenced. These sequences have shown striking similarities with a human lymphoid cell activation antigen named CD39 (Maliszenski et al., 1994). Since the molecular weight of CD39 and its glycosylation rate appears to define a human counterpart for the present bovine aortic ATPDase, it is the first time that a sequence is assigned to an ATPDase. A process of producing an ATPDase by recombinant technology is now possible using a host cell expressing the CD39 human protein, its homologous sequences in bovine and porcine species, and variants and parts thereof.

The present invention also relates to the use of CD39 and of the above bovine and porcine homologous proteins for reducing platelet aggregation and thrombogenicity.

DESCRIPTION OF THE PRESENT INVENTION

The research team to which the present inventors belong has already characterized the pig pancreatic ATPDase, and the latter reassessed the properties of the bovine aorta enzyme. They confirmed that the aorta ATPDase was different from its pancreatic counterpart. They have found previously (Côté et al., 1992) that the aorta enzyme (isolated from a microsomal fraction of the cells) had a molecular weight of about 190 kDa in its native state. In their work for extensively purify this enzyme, they found that the highly purified enzyme had a molecular weight on SDS-PAGE of about 78 KDa. Yagi et al. (1989) have already shown that an ATPDase purified to homogeneity had a molecular weight of 110 KDa. After purifying the enzyme by the present method, the 110 kDa band was indeed absent from SDS-PAGE. A unique band migrating of an estimated weight of 78 KDa was rather revealed. The confirmation of the identity of the purified enzyme was achieved by binding FSBA, an ATP analog binding the enzyme, to the separated and blotted enzyme. The use of anti-FSBA antibodies revealed the presence of the bound enzyme and this binding was inhibited with ATP and ADP. The same procedure was applied to confirm the identification of the pancreas ATPDase Type I.

The present process allows the purification of ATPDases to a very high level. In the aorta, the purified enzyme has a specific activity which is increased by at least 300 fold compared with the specific activity of microsomal fraction (already enriched by about 30 fold from the crude cell preparation).

The bovine aorta and porcine pancreatic ATPDases have been partially sequenced, and the sequences have been found to be highly homologous to a human lymphoid cell activation antigen designated CD39 (Maliszenski et al.,op. cit.). The complete sequences of the ATPDases types I and II have not been obtained yet. If one assumes that CD39 gene product is an ATPDase type II, the present invention therefore contemplates the use of CD39 in the reduction of platelet aggregation and of thrombogenicity, as well as a process of making ATPDases using the CD39 sequence, variants or parts thereof (recombinant technology).

The present invention will be described hereinbelow with reference to the following Examples and Figures which purpose is to illustrate rather than to limit the scope of the present invention.

EXAMPLE 1

Figure 1:
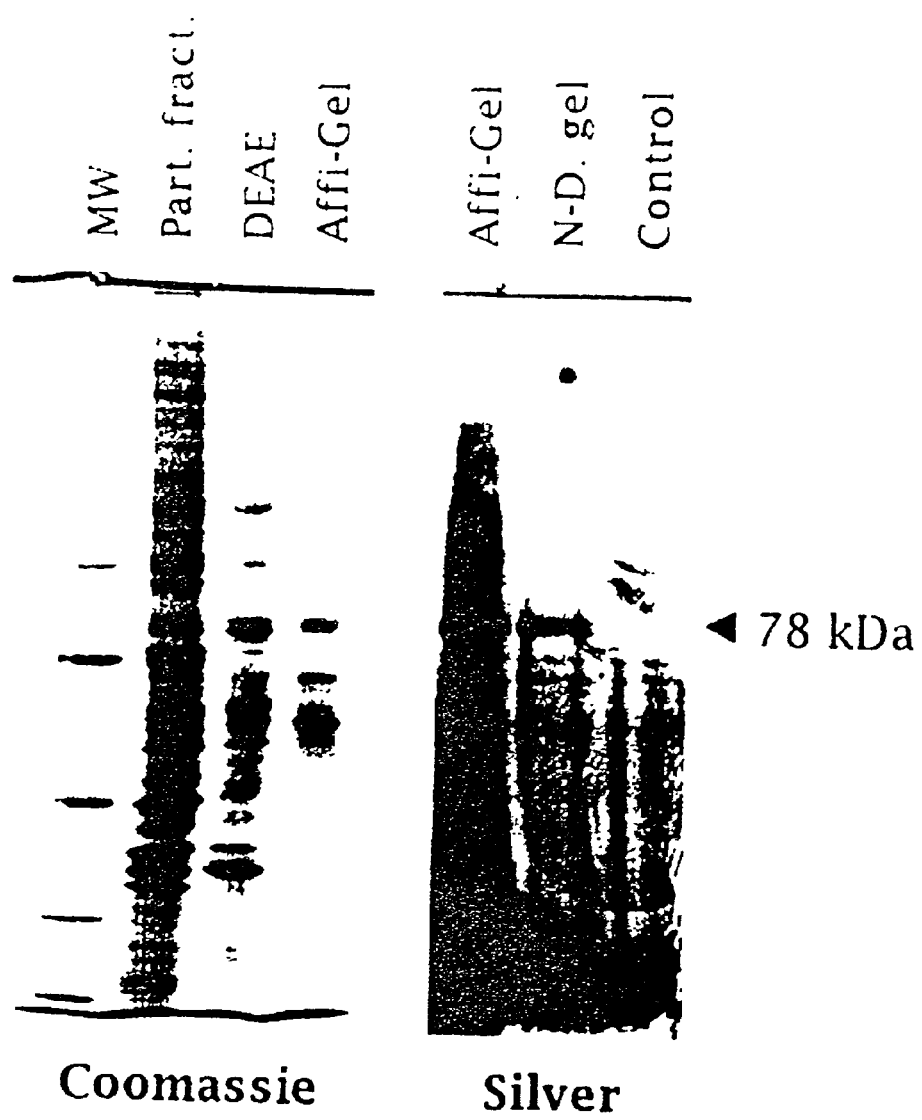
FIG. 1 illustrates the protein composition of the bovine aorta ATPDase (type II) at the different purification steps as determined by SDS-PAGE. Electrophoresis was run in a 7–12.5% polyacrylamide gel. Proteins were stained with Coomassie Blue or silver nitrate dye. MW standards: 97.4, 66.2, 45.0, 31.0, 21.5, 14.4 KDa; particulate fraction (part. fract.), 100 µg; DEAE-agarose fraction, 35 µg; Affi-Gel blue fraction, 20 µg; the lower band of activity was cut out from the non-denaturing gel (N.D. gel); sample buffer alone (Control).

Purification of the ATPDase Type II a) Isolation of the Particulate (Microsomal) Fraction from the Bovine Aorta Bovine aorta, obtained from a local slaughterhouse, were kept on ice and processed within one hour after the death of the animals. All steps were carried out at 4° C. The inner layer was stripped out manually, passed through a meat grinder, and homogenized (10%) with a Polytron™ in the following solution: 95 mM NaCl, Soybean Trypsin Inhibitor (20 µg/mL), 0.1 mM Phenyl-methyl-sulphonyl-fluoride (PMSF) and 45 mM Tris-HCl pH 7.6. After filtering with cheesecloth, the homogenate was centrifuged at 600 X g for 15 minutes with a Beckman JA-14 centrifuge at 2100 RPM. The supernatant was recovered and centrifuged at 22,000 X g for 90 minutes with the same centrifuge at 12,000 RPM. The resulting pellet was suspended in 0.1 mM PMSF and 1 mM $NaHCO_3$ pH 10.0 with a Potter Elvejehm™ homogenizer at a dilution of 3 to 6 mg of protein per mL. The suspension was loaded on a 40% sucrose cushion and centrifuged at 100,000 X g for 140 minutes with a SW 28 Beckman rotor. The enzyme was recovered on the cushion and kept at 4° C. overnight. This membrane preparation was then suspended in 12 volumes of 0.1 mM PMSF and 1 mM $NaHCO_3$ pH 10.0 and centrifuged at 240,000 X g for 45 minutes in a SW 50.2 Beckman rotor. The pellet was rinsed twice: once with o 0.1 mM PMSF and 30 mM Tris-HCl ph 8.0 and once with 2 mM EDTA and 30 mM Tris-HCl pH 8.0. The final pellet was suspended in 7.5% glycerin and 5 mM Tris-HCl ph 8.0 at a concentration>1 mg of protein per mL and frozen at −20° C., or directly solubilized. At this stage, the specific activity of the ATPDase was enriched by about 33 fold.

b) Solubilization and Column Chromatographies

The particulate fraction (pf) was solubilized with 0.3% Triton X-100™ and 30 mM Tris-HCl pH 8.0 at a concentration of 1 mg/mL protein and centrifuged at 100,000 X g for 1 hour in a SW 50.2 Beckman rotor. All further steps involving a detergent are practised with Triton X-100, but any similar detergent (a non-ionic detergent) may be used for achieving the purpose of this invention. The supernatant was loaded on an ion exchange column, preferably containing diethylaminoethyl (DEAE), like DEAE-Bio Gel A Agarose™, preequilibrated with 0.1% Triton X-100™, 7.5% glycerin and 10 mM Tris-HCl pH 8.0. The protein was eluted in the same buffer by a NaCl gradient (0.03 to 0.12 M), followed by a 0.1% Triton X-100™ and 2 M NaCl wash. Active fractions were pooled in 0.1X buffer E (5X buffer E: 0.5% Triton X-100™, 960 mM glycine, 125 mM Tris-HCl pH 7.0) and electrodialysed in 15 mL cuvettes by an ISCO™ electro-eluter according to the following technique: 1X buffer E was loaded in the apparatus and a 15 mA current was applied per cuvette. The 1X buffer E was changed 4 times at 50 minute intervals. The dialysate was equilibrated at pH 5.9 with 200 mM histidine adjusted to pH 4.0 with HCl (about 20 mM final) and loaded on an Affi-Gel™ blue column preequilibrated with 0.07% Triton X-100™, 7.5% glycerin, 30 mM histidine and 30 mM Tris-HCl pH 5.9. Proteins were eluted by a linear gradient from 100% buffer A to 100% buffer B (buffer A (80 ml): 0.07% Triton X-100™, 7.5% glycerin and 10 mM Tris-HCl pH 6.5; buffer B (80 ml): 1M NaCl, 0.07% Triton X-100™, 7.5% glycerin and 10 mM Tris-HCl pH 7.5), followed by a 1M NaCl, 0.1% Triton X-100™, 100 mM Tris-HCl pH 8.5 wash. The active fraction was dialysed against 0.05% Triton X-100™, 1 mM Tris-HCl pH 8.0, concentrated on a 1 ml DEAE-agarose column as described above, eluted in 0.4 M NaCl, 0.07% Triton X-100™, 10 mM Tris-HCl pH 8.0 and dialysed against distilled water.

c) Separation by Polyacrylamide Gel Electrophoresis (PAGE) under Non-denaturing Conditions This type of gel allows for separating proteins upon their molecular weight and electrical charge while preserving their activity in such a way that this activity can be measured after migration. Two polyacrylamide preparations were poured between two glass plates to form a gradient and polymerized. The 4% acrylamide solution was composed of: 4.5 mL of separating buffer (Tris 1.5 M pH 8.8+0.4% Triton X-100™), 2.5 mL acrylamide 30%, 180 µL Na deoxycholate 10%, water up to 18 mL, 60 µL APS 10% and 7 µL TEMED. The 7.5% acrylamide solution was composed of the same ingredients except for the volume of acrylamide: 4.5 mL. A stacking gel was extemporaneously prepared and poured at the top of the separating gel, the stacking gel was composed of: 2.5 mL of stacking buffer (Tris-base 0.5 M pH 6.8), 6.1 mL of water, 1.34 acrylamide 30%, 0.1 mL Na deoxycholate 10%, 0.1 mL Triton X-100™, 50 µL APS 10% and 10 µL TEMED. Wells are formed in this layer during polymerization. Two volumes of the sample obtained after DEAE-agarose or Affigel Blue columns were added to one volume of sample buffer of the following composition to obtain about 100 µg proteins: 0.07% (v/v) Triton X-100™, 1.5% (w/v) Na deoxycholate, 10% glycerol, 65 mM Tris-base and 0.005% bromophenol blue. The suspended sample was allowed to stand 10 minutes on ice and centrifuged. The supernatant was loaded on gel. The proteins were migrated at 4° C. at a 20 mAmp power in reservoir buffer (0.1% Triton X-100, 0.1% sodium deoxycholate, 192 mM glycine and 25 mM Tris pH 8.3). For revealing activity in the separated bands, the latter were placed in a dosage buffer (Tris-base 66.7 mM, imidazole 66.7 mM, $CaCl_2$ 10 mM, pH 7.5). After preliminary incubation for 30 minutes at 37° C., the substrate (ADP or ATP) 5 mM was added. After 2 to 10 minute incubation, a white calcium phosphate precipitate significative of ATP diphosphohydrolase activity is formed. Three bands are seen for the aorta enzyme and one for the pancreas (these bands were all revealed on gel by silver overstaining). For further characterization, the most active band was loaded on an SDS-PAGE according to Laemmli (1970) and a single band appeared on the gel after silver nitrate staining, which is indicative of an enzyme purification to homogeneity after the non-denaturing gel. FIG. 1 shows the high sensitivity of detection conferred by the use of silver staining compared to a conventional Coomassie blue staining (see lanes 4 and 5). The active band purified from the gel has a molecular weight of 78 KDa when migrated on SDS-PAGE.

d) ATPDase Assays during Chromatographic Steps

Enzyme activity was determined at 37° C. in the following incubation medium: 50 mM Tris-imidazole (pH 7.5), 8 mM $CaCl_2$ and 0.2 mM substrate (ATP or ADP). Phosphorus was measured by the malachite green method according to Baykov et al. (1988). One unit of enzyme corresponds to the liberation of 1 µmol of phosphate per minute per mg of protein at 37° C. Proteins were estimated by the technique of Bradford (1976).

The ATPDase activity retrieved in isolated fractions are summarized in the following Table:

TABLE 1

ATPDase purification of the bovine aorta ATPDase type II

| Step | Total protein mg | Total activity units | Specific activity units/mg | Yield % | Purification factor -fold | Hydrolysis rate ATP/ADP |
|---|---|---|---|---|---|---|
| Particulate fraction (pf) | 293 | 263 | 0.9 | — | (33)* | 1.5 |
| pf + Triton X-100 | 293 | 117 | 0.4 | 100 | 1 | 1.4 |
| 100,000 g supernatant of solubilized pf | 186 | 91.2 | 0.5 | 78 | 1.2 | 1.3 |
| DEAE column | 15.1 | 72.2 | 4.8 | 62 | 11.9 | 1.1 |
| Affi-Gel blue column | 2.76 | 57.8 | 21 | 49 | 53 | 1.1 |
| Con A | 0.61 | 33.5 | 55 | 29 | 138 | 1.1 |

Details on the purification and condition assays are described in the disclosure. A representative out of five complete purification procedures is shown with ADP as substrate. Determinations were routinely carried out in triplicate.
*The starting particulate fraction shows a 33 purification folds as compared to the homogenate (Côté 1991).

e) Confirmation of the Identity of ATPDase

Figure 2:
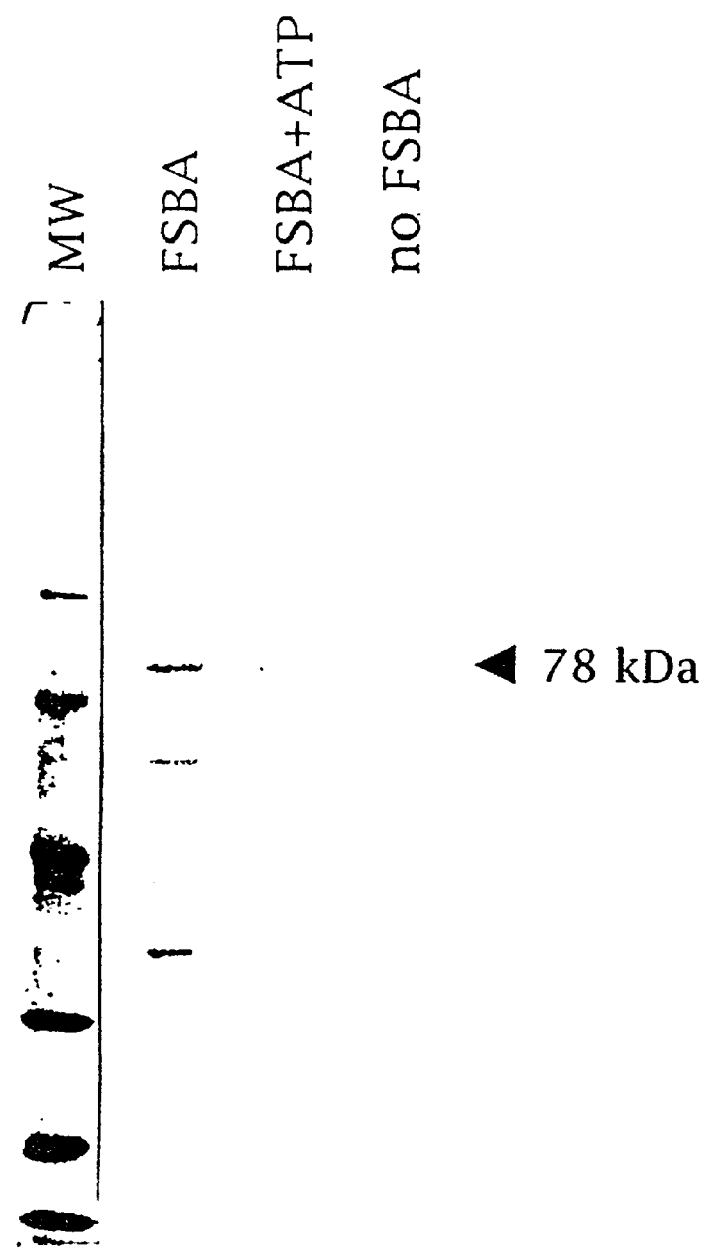
FIG. 2 illustrates a Western blot of FBSA labelled protein (ATPDase type II) isolated from Affi-Gel blue column. Labelled proteins were separated on a 8–13.5% gradient gel by SDS-PAGE, transferred to Immobilon-P membrane, incubated with a rabbit antibody anti-FBSA (1:10,000) and detected by a secondary antibody conjugated to alkaline phosphatase (1:6,000). Twenty µg of protein from Affi-Gel blue column fraction was used for the assays: incubation with FBSA (FBSA); incubation with FBSA with competing Ca-ATP (FBSA+ATP); incubation without FBSA (no FBSA). MW standards are the same as in FIG. 1.
Figure 3:
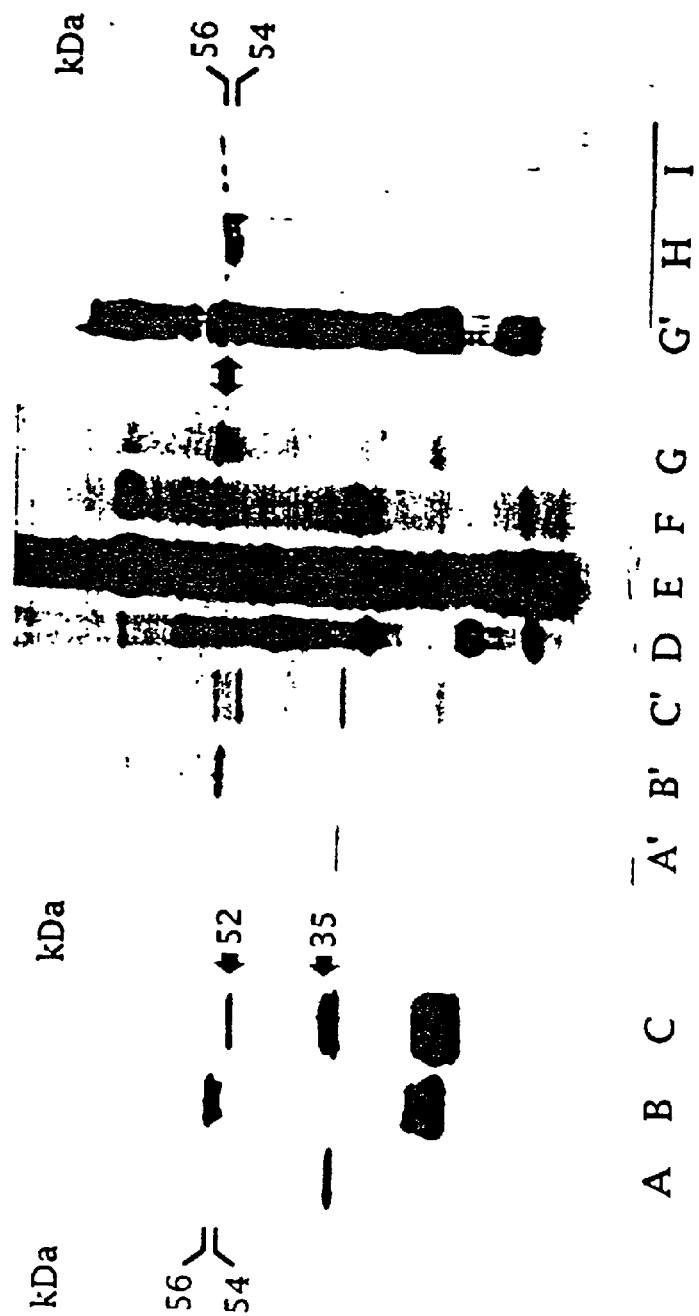
FIG. 3 illustrates the SDS-PAGE protein patterns at the different steps of the purification procedure and after N-glycosidase F digestion of the Affi-Gel blue fraction. Protein samples were fractionated on a 8–13.5% polyacrylamide gradient. A) One unit of N-glycosidase F (silver nitrate stain); B) Six µg from the Affi-Gel blue fraction incubated for 12 h without N-glycosidase F (silver nitrate stain); C) Idem as B with 1 unit of N-glycosidase F (silver nitrate stain); A') Same as A (Coomassie blue stain); B') Same as B (Coomassie blue stain); C') Same as C (Coomassie blue stain); D) MW standards: 97.4, 66.2, 45.0, 31.0, 21.5, 14.4 kDa (Coomassie blue stain), E) ZGM (zymogen granule membrane), 60 µg (Coomassie blue stain); F) Active fraction from DEAE-agarose column, 25 µg (Coomassie blue stain); G) Active fraction from Affi-Gel blue column, 6 µg (Coomassie blue stain); G') Same as G (silver nitrate overstain); H) Activity band located after PAGE under non-denaturing conditions (silver nitrate overstain); I) Control, band located just above the activity band after PAGE under non-denaturing conditions (silver nitrate overstain).
Figure 4:
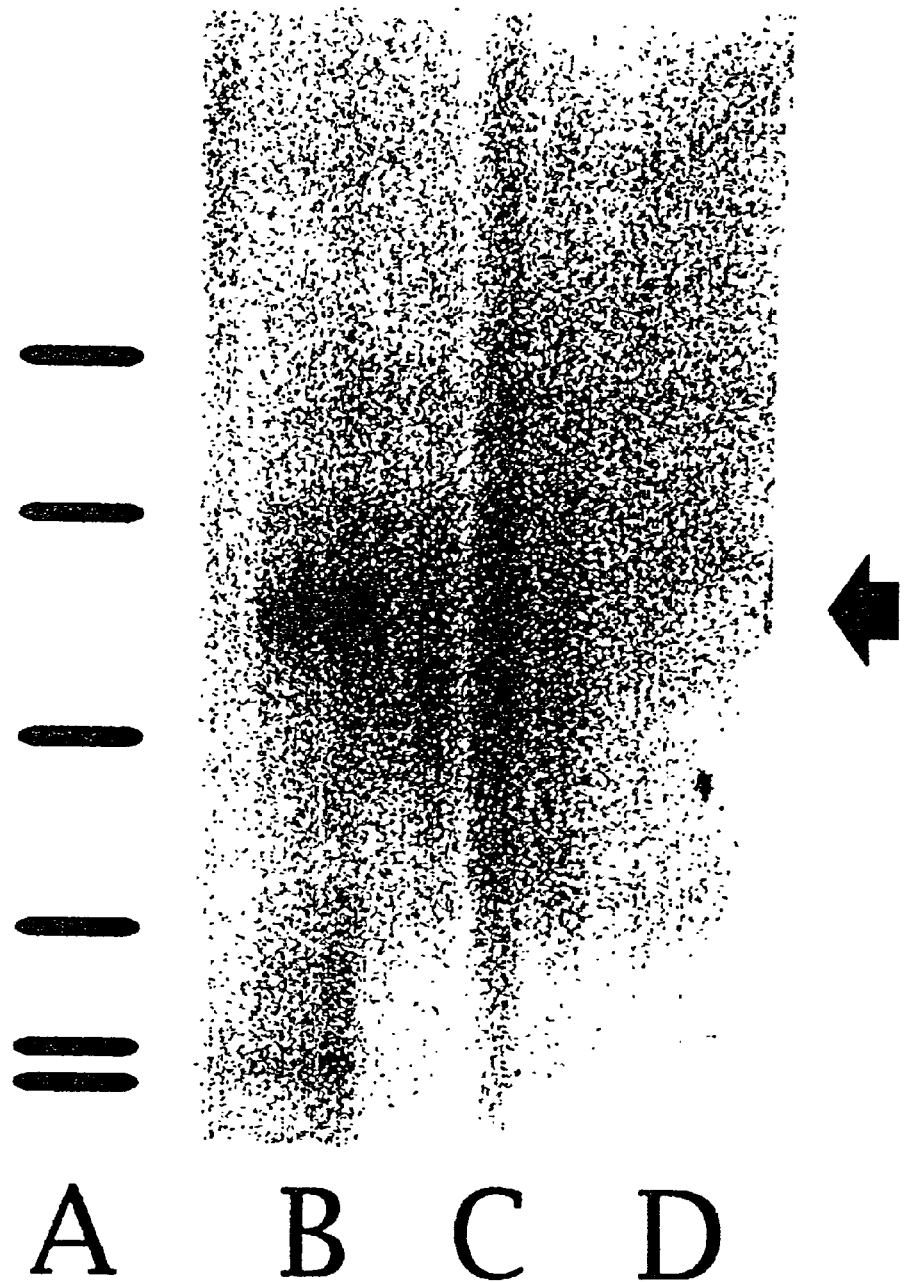
FIG. 4 shows a Western blot of FSBA labelled samples of the pancreatic enzyme type I fraction. Labelled sample were loaded on a 7–12% polyacrylamide SDS-gel, transferred to Immobilon-P membrane, incubated with the rabbit antibody anti-FSBA and detected by a secondary antibody conjugated to alkaline phosphatase. Six µg of Affi-Gel blue column were used in lanes B), C) and D). A) MW standards: 97.4, 66.2, 45.0, 31.0, 21.5, 14.4 kDa; B) FSBA; C) FSBA+competing ADP; D) No labelling.

The fraction eluted from Affi-gel was labelled with 5′-p-fluorosulfonylbenzoyl adenosine (FBSA), a marker which forms covalent bonds with adenosine-binding proteins. FSBA blocked the enzyme activity and excess of ATP or of ADP prevents this effect. In addition, FSBA efficiently bound the purified enzyme, as monitored by a Western blot technique using an antibody directed to FSBA, which binding is prevented in the presence of ATP (see FIG. 2) or ADP (data not shown).

The results obtained on SDS-PAGE shows that the enzyme was purified to homogeneity when using the successive steps of solubilization of the particulate fraction, first purification on an ion exchange column, second purification on an affinity column and third purification on non-denaturing electrophoretic conditions. The Affigel Blue column did not achieve purification to homogeneity but allowed a much higher recovery then the 5′ AMP-Sepharose™ used by Yagi et al. (about 7 fold higher). Moreover, the use of the Affigel column and the non-denaturing gel allowed us to purify an enzyme that is different from the one disclosed by Yagi.

f) ATPDases are Glycosylated Proteins

Purification on Concanavalin A column

Further purification of the Affi-Gel blue fraction of aorta enzyme was also obtained with Con A agarose column. Briefly, Con A (4 ml beads) and the protein sample from the Affi-Gel blue column were preequilibrated with 0.05% Triton X-100, 100 mM NaCl, 1 mM $CaCl_2$, 1 mM $MnCl_2$ and 20 mM PIPES, pH 6.8, at room temperature. The protein sample was passed through the column at a flow rate of 3 ml/h, 40 ml of the preequilibration buffer was then added to wash the unbound materials at a flow rate of 10 ml/h. The activity was eluted with 20 ml of 0.5 M Me-α-D-mannopyranoside diluted in the preequilibration buffer. The purified sample was dialysed and concentrated on a mini-DEAE column as described above.

Precipitation of ATPDase Activity with Lectin-agarose

Four lectins conjugated to agarose were tried: Con A, WGA, Soybean agglutinin and UEA. Experiments were carried out at room temperature for Con A, and at 4° C. for the other agglutinins. One hundred µl of each 50% slurry were put in a microcentrifuge tube and washed 4 times with buffer A: 0.05% Triton X-100, 100 mM NaCl and 20 mM PIPES pH 6.8. In the case of Con A, 1 mM $CaCl_2$ and 1 mM $MnCl_2$ were added to this buffer. Twenty µg of ATPDase purified from the Affi-Gel blue column, equilibrated in buffer A, were added to the lectin-agarose beads and rocked for 45 min, then centrifuged for 1 min. The supernatant was kept and the beads were washed 3 times with 1 ml buffer A. Protein bound to the lectins was eluted with 150 µl of 500 mM of the appropriate sugar in buffer A, rocked for 30 min and centrifuged. The elution step was repeated once and the 2 eluates were pooled. The sugar used to eluate proteins from Con A, WGA, Soybean and UEA were Me-α-D-mannopyranoside, D-GlcNAc, D-GalNAc and L-Fuc respectively.

TABLE 2

ATPase binding to lectins

| Lectin-agarose | Fractions | Relative ADPase activity | Presence of the 78 kDa band on SDS-PAGE | Sugar specificity |
|---|---|---|---|---|
| Con A | Supernatant | 5% | traces | Mannose, |
|  | Bound | 95% |  | Glucose |
|  | Eluted | 62% | + |  |
| WGA | Supernatant | 5% | traces | GlcNAc, NeuNAc, |
|  | Bound | 95% |  | Mannose structure § |
|  | Eluted | 69% | + | Sialic acid § |
| Soybean | Supernatant | 100% | + | GalNAc |
|  | Bound | 0% |  |  |
|  | Eluted | 0% | — |  |

TABLE 2-continued

ATPase binding to lectins

| Lectin-agarose | Fractions | Relative ADPase activity | Presence of the 78 kDa band on SDS-PAGE | Sugar specificity |
|---|---|---|---|---|
| UEA | Supernatant | 100% | + | Fucose |
|  | Bound | 0% |  |  |
|  | Eluted | 0% | − |  |

Twenty μg of ATDPase fraction purified by Affi-Gel blue chromatography were incubated separately with four lectins conjugated to agarose, centrifuged, and the supernatants were collected. Lectins-agarose beads were then washed. Bound proteins were finally eluted with the appropriate sugar as described in the disclosure. This experiment has been done twice in triplicate and the mean is presented. In parallel, the supernatant and the eluted fraction were put on SDS-PAGE, stained with silver nitrate, and looked for the presence of the 78 kDa. The sugar specificity of each agglutinin is also presented.
§ Weak affinities Only WGA bound the ATPDase type II as for Con A. ATPDase binding to these two lectins is indicative of a specificity for the sugars glucose and/or mannose and/or GlcNAc (Glucosamine-N-Acetyl) and/or NeuNAc (Neuraminic-N-Acetyl).

The deglycosylated form had a molecular weight of about 56 KDa, which suggests that about 5 to 11 glycosyl chains are present on the 78 KDa protein (assuming that a glycosyl group may have a molecular weight of 2 to 4 KDa).

Example 2
Purification of the ATPDase Type I

The procedure described in Example 1 has been followed for purifying the pancreatic ATPDase type I enzyme, starting from the zymogen granule membrane of pig pancreas.

In deglycosylation experiments, the molecular weight of the catalytic unit has been shown to be shifted from 54 to 35 KDa. Therefore, the chemical procedure exemplified above is deemed to apply to the purification of ATPDases in general.

b) Level of Enrichment

The level of enrichment is determined from the data shown in Table 1 for aorta ATPDase type II and from the following Table 3 obtained for pancreatic ATPDase type From the crude cell preparation to the Affigel Blue column, the enzymes of both pancreatic and aorta sources were purified to at least a 1600 fold level (see Tables 1 and 3. After the non-denaturing gel, the quantity of proteins falls under the detection level of the method used, which renders difficult the calculation of a specific activity. However, one can roughly estimate the process to reach about a 10 thousand fold purification, as judged by the density of the ATPDase reaction band relative to other proteins on the non-denaturing electrophoretic gel.

Referring to Table 1, the lectin-binding step is not considered properly as an essential step of the purification process. This step has been added to show that the aorta ATPDase is a glycoprotein which, when deglycosylated, shifts from a molecular weight of 78 KDa to a molecular of 56 KDa (representing the proteic backbone). Since the lectin-binding step does not achieve the obtention of a pure protein, the most convenient way to obtain a pure protein is to submit the crude cell preparation sequentially to the ion exchange chromatography, the Affigel Blue chromatography and to non-denaturing gel electrophoresis. The identity of the protein is then confirmed by ATP-labelling with FSBA.

Example 3
Partial Amino Acid Sequences

CNBr digests have been obtained from the purified bovine aorta and porcine pancreatic ATPDases. The sequences of the digests are as follows:

|  | SEQ. ID. NO.: |
|---|---|
| Bovine aorta ATPDase: |  |
| Glu Thr Pro Val Tyr Leu Gly Ala Thr Ala Gly | 3 |
| Leu Leu Arg Met Glu | 4 |
| Ala Asp Lys Ile Leu Ala Asn Xaa Val Ala | 5 |
| Ser Ser Ile |  |
| Tyr Pro Phe Asp Phe Gln Gly Ala Arg Ile | 6 |
| Porcine pancreatic ATPDase: |  |
| Lys Ser Asp Thr Gln Glu Thr Tyr Gly Ala | 7 |
| Leu Asp Leu Gly Gly Ala Ser Thr Gln Val |  |

When compared to the sequence which accession number is G2345 (CD39 gene product; Maliszenski et al. 1994), the above partial sequences show a very high degree of homology. The following differences are however found with the CD39 sequence:

In the porcine pancreatic enzyme, $Gln^{202}$ is changed to Lys, the $Asn^{204}$ is changed to Asp, $Asn^{205}$ is changed to Thr.

In the bovine aortic enzyme, $Arg^{147}$ is changed to Lys, $Val^{148}$ is changed to Ile, $Asp^{150}$ is changed to Ala, $Gln^{153}$ is changed to Ala, $Arg^{154}$ is changed to Ser, and $Leu^{156}$ is changed to Ile.

The human CD39 has a predicted molecular weight of 57 KDa, while the apparent molecular of this protein is 78 KDa on SDS-PAGE.

Both ATPDases type I and II share a high degree of homology with CD39 for the compared sequenced fragments. CD39 appears to be a human enzyme corresponding to the bovine aortic ATPDase. It is worthwhile noting that the first N-terminal 200 amino acids of CD39 are absent from the ATPDase type I (pancreatic enzyme). This suggests that the active site of ATPDases is located between the residues 200–510 of CD39 and that part of CD39 is sufficient to provide this activity. It is further worthwhile noting that exact correspondence between the two ATPDases of this invention and the already described ATPDases cannot be established. The human placenta ATPDase (Christoforidis et al. 1995) has a molecular weight of 82 KDa while CD39 (also of human origin) has a molecular weight of 78 KDa. Due to the differences found in diverse tissues of the same species, extrapolation cannot be done to the effect that the bovine aorta enzyme of this invention is one of the already described enzymes. The obtained partial amino acid sequences indeed already shown differences of sequences which may affect some of the physico-chemical properties of the claimed enzymes when compared to their human counterparts (some of the above-observed substitutions are not conservative ones; the net charge of the enzymes may not be the same and the substituted amino acids may change the behaviour of the enzymes (optimum pH, sensitivity towards inhibitors, etc . . . ).

Cross-reactivity between ATPDases I and II

Antibodies were produced in rabbits against the following amino acid sequence which is common to ATPDase I and CD39:

|  | SEQ. ID. NO.: |
|---|---|
| Lys Ser Asp Thr Gln Glu Thr Tyr Gly Ala 5 10 | 8 |
| Leu Asp Leu Gly Gly Ala 15 | |

Figure 5:
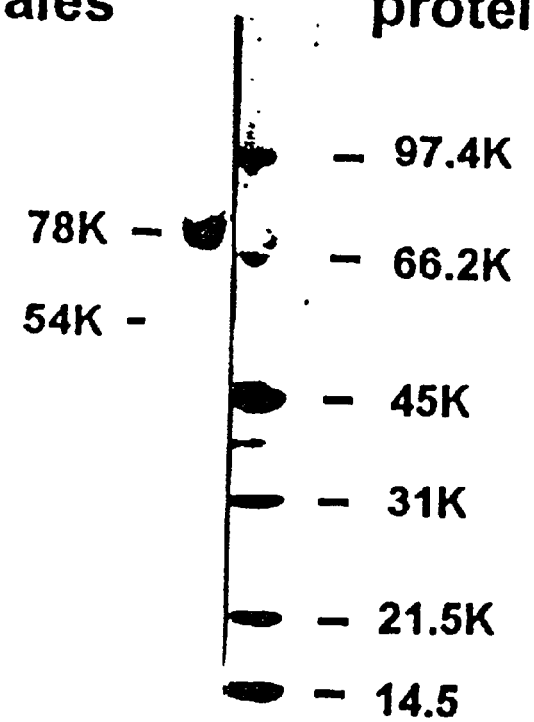
FIG. 5 shows a Western blot of human endothelial cell extracts labelled with an antibody directed against a fragment common to ATPDase type I and CD39. The ATPDase type II (78 KDa) is clearly detected as well as low amounts of ATPDase type I (54 KDa).

FIG. 5 shows that these antibodies reacted positively with a 78 KDa protein present in endothelial extracts of human sources. They also reacted with a protein of 78 KDa of a bovine aorta extract (data not shown). This is an indication that ATPDases I and II share homology of sequence, and that the latter comprises the peptidic sequence of SEQ. ID. No.: 8 or a variant thereof.

A type I ATPDase appears to be present in low amounts in endothelial cells as shown by the detection of a faint band corresponding to this protein (54 KDa) in FIG. 5.

Conclusions

Considering that the ATPDase has an antihemostatic role in the saliva of blood-feeding insects and leeches (Rigbi et al., 1987);

considering that Côté et al. (1992) have demonstrated bovine ATPDase type II has platelet anti-aggregant properties by converting ADP to AMP;

considering the low Km of the aorta type II enzyme ($\mu$M), the optimum pH of catalysis pH 7.5–8.0, its localization at the surface of endothelial and smooth muscle cells of blood vessels (Côté et al., 1992);

considering that the purified enzyme keeps its original characteristics;

it sounds predictable that the aorta enzyme produced in the present invention can be introduced in the circulatory system of mammalians to reduce platelet aggregation and thrombogenicity.

Furthermore, considering that a crude microsomal bovine ATPDase type II fraction has been successfully conjugated to agarose and that the conjugate could reduce ADP induced platelet aggregation (Hirota et al., 1987);

considering that a semi-purified plant ATPDase has been successfully coupled to the following matrices: CM-cellulose, copolymers of L-alanine and L-glutamic acid, polyaspartic acid, polygalacturonic acid, Elvacite 2008™ (methyl methacrylate) and ethylene-maleic acid co-polymer (Patel et al., 1969);

we propose that the purified ATPDase type II can be coupled to artificial polymers/biomaterials to reduce thrombogenicity (platelet aggregation).

Therefore, pharmaceutical compositions for use in the reduction of platelet aggregation and thrombogenicity are under the scope of the invention. These compositions should contain, as an active ingredient, the ATPDase type II of this invention combined to an acceptable carrier without excluding any form or formulation of such compositions. Finally, considering that the sequenced CD39 appears to correspond to a human counterpart of the bovine ATPDase type II enzyme of this invention, the use of CD39 or variants or a part thereof for reducing platelet aggregation and thrombogenicity is also part of this invention.

A new process for producing an ATPDase comprising the steps of:

obtaining a host which comprises a nucleic acid encoding a protein having the amino acid sequence defined in SEQ. ID. NO.: 1, or a variant thereof, or a part thereof, said variant or part being capable of converting ATP to ADP and ADP to AMP;

culturing said host in a culture medium supporting the growth of said host and the expression of said nucleic acid;

recovering the ATP diphosphohydrolase from the culture medium or from said host; and purifying the ATP diphosphohydrolase is also part of the invention. Preferably the nucleic acid is the one defined in SEQ ID NO.: 2, or a part or a variant thereof, which part or variant is capable of producing an ATP diphosphohydrolase.

The present invention has been described hereinabove; it will become apparent to the skilled reader that variations could be brought thereto without departing from the teachings of the present disclosure. Such variations are under the scope of this invention.

TABLE 3

ATPDase purification

| Steps | Total protein mg | Total activity units | Specific activity (ATP) units/mg | Yield % | Purification factor fold | Hydrolysis rates ATP/ADP |
|---|---|---|---|---|---|---|
| ZGM | 20.0 | 60.8 | 3.0 | — | (160) * | 1.3 |
| ZGM + Triton X-100 | 20.0 | 40.6 | 2.0 | 100 | 1 | 1.3 |
| 100,000 g supernatant of solubilized ZGM | 17.6 | 37.0 | 2.1 | 91 | 1.1 | 1.3 |
| DEAE column | 3.5 | 28.8 | 8.3 | 71 | 4.2 | 1.3 |
| Affi-Gel blue column | 0.31 | 13.8 | 45 | 34 | 23 | 1.3 |

Results of one out of three preparations is presented. Determinations were carried out in triplicate.
* Laliberte et al. showed a 160 fold purification for the ZGM as compared to the homogenate using ADP as the substrate.

Bibliography
Baykov et al. (1988). Anal. Biochem. 171:266–270.
Bradford, M (1976). Anal. Biochem. 72:248–254.
Côté et al. (1991). BBA 1078:187–191.
Côté et al. (1992). BBA 1139:133–142.
Christoforidis et al. (1995), Eur. J. Biochem. 234:66–74.
Hirota et al. (1987). Thrombosis Res. 45:201–209.
Laemmli (1970). Nature 227:680–685.
Lebel et al. (1980). J. Biol. Chem. 255:1227–1233.
Maliszewski et al. (1994). J. Immunol. :3574–3583
Patel et al. (1969). BBA 178:626–629.
Rigbi et al. (1987). Comp. Biochem. Physiol. 87B:567–573.
Yagi et al. (1989). Eur. J. Biochem. 180:509–513.

What is claimed is:

1. An isolated and purified ATP diphosphohydrolase obtainable from a mammalian tissue characterized by the following physico-chemical properties:
   a catalytic unit of a molecular weight on denaturing polyacrylamide gel electrophoresis of about 54 KDa;
   a deglycosylated form of said catalytic unit of a molecular weight on SDS-PAGE of about 35 KDa; and
   characterized in that it comprises the amino acid sequence defined in SEQ. ID. NO:7.

2. A method for reducing platelet aggregation and thrombogenicity in a human or nonhuman animal comprising the step of treating with an effective amount of the ATP disphosphohydrolase of claim 1 sufficiently to reduce platelet aggregation and thrombegenicity in the human or nonhuman animal.

3. A process for purifying an ATP-diphosphohydrolase enzyme from a tissue capable to convert ATP to ADP and ADP to AMP which comprises:

a) obtaining a subcellular microsomal fraction from an homogenate of said tissue;

b) solubilizing said microsomal fraction in the presence of a non-ionic detergent;

c) centrifuging said solubilized microsomal fraction to obtain a supernatant containing said enzyme;

d) submitting said supernatant to an ion-exchange chromatography to obtain a first enzyme eluate;

e) submitting said first eluate to an affinity column chromatography to obtain a second enzyme eluate; and f) submitting said second eluate to a separation step on a non-denaturing gel electrophoresis to recover said enzyme free of any contaminant, the presence of said contaminant being monitored by overstaining said gel in a silver nitrate dye or Coomassie Blue dye, whereby an isolated and purified ATP diphosphohydrolase according to claim 1 is obtained.

4. A process according to claim 3 wherein said ion exchange chromatography is achieved on a column containing Diethylaminoethyl (DEAE).

5. A process according to claim 4 wherein said column is a DEAE agarose column.

6. A process according to claim 3 wherein an aliquot of said enzyme is further submitted after step f) to a polyacylamide gel electrophoresis under denaturing conditions to verify its homogeneity and to obtain its apparent molecular weight.

7. A process according to claim 3 wherein said enzyme is obtained from pig pancreatic zymogen granules and has an apparent molecular weight of about 54 Kilodaltons.

8. A process according to claim 7 wherein, between steps e) and f), a step of deglycosylation is included, and whereby the apparent molecular weight is shifted from 54 to 35 KDa.

9. A method for reducing platelet aggregation and thrombogenicity comprising an administration of the ATP diphosphohydrolase of claim 1.

10. A method for reducing platelet aggregation and thrombogenicity comprising an administration of an ATP diphosphohydrolase comprising the amino acid sequence defined in SEQ ID NO:7.

11. A composition for reducing platelet aggregation and thrombogenicity which comprises as an active ingredient the ATP diphosphohydrolase of claim 1, together with an acceptable pharmaceutical carrier.

12. An aggregation and thrombogenicity-reducing composition, which comprises as an active ingredient the mammalian ATP diphosphohydrolase of claim 1, together with a pharmaceutically acceptable carrier.

13. A composition for converting ATP into ADP and/or ADP into AMP, which comprises as an active ingredient the mammalian ATP diphosphohydrolase of claim 1, together with a pharmaceutically acceptable carrier.

14. A process for purifying an ATP diphosphohydrolase enzyme which can convert ATP to ADP and/or ADP to AMP, said process comprising:

a) separating a crude fraction of said enzyme from contaminating material by centrifugation;

b) submitting said enzyme of a) to at least one of ion-exchange chromatography and affinity column chromatography to obtain a purified enzyme eluate;

whereby an isolated and purified ATP diphosphohydrolase according to claim 1 is obtained.

15. The process of claim 14, wherein said crude fraction is incubated with a non-ionic detergent, prior to centrifugation.

16. The process of claim 15, wherein said enzyme of a) is submitted to at least one round of ion-exchange chromatography to yield a first enzyme eluate, and said first enzyme eluate is submitted to at least one round of affinity chromatography, to yield a second enzyme eluate.

17. The process of claim 16, wherein said second enzyme eluate is electrophoresed on a non-denaturing gel, thereby recovering substantially pure ATP diphosphohydrolase, and wherein a presence of contaminants in said substantially pure ATP diphosphohydrolase can be monitored by overstaining said non-denaturing gel in a silver nitrate dye or Coomassie Blue dye.

18. The process of claim 17, wherein said ion exchange chromatography is achieved on a Diethylaminoethyl (DEAE) column.

19. The process of claim 18, wherein said column is a DEAE agarose column.

20. The process of claim 14, wherein said enzyme is obtained from a mammalian membrane preparation and has an apparent molecular weight of about 54 Kilodaltons.

21. A substantially pure mammalian ATP diphosphohydrolase characterized by the following physico-chemical properties:

a catalytic unit of a molecular weight on denaturing polyacrylamide gel electrophoresis of about 54 KDa;

a deglycosylated form of said catalytic unit of a molecular weight on SDS-PAGE of about 35 Kda.

22. A composition for use in the reduction of platelet aggregation and thrombogenicity comprising as an active ingredient the substantially pure mammalian ATP diphosphohydrolase of claim 21, together with a pharmaceutically acceptable carrier.

23. A composition for converting ATP into ADP and/or ADP into AMP comprising as an active ingredient the substantially pure mammalian ATP diphosphohydrolase of claim 21, together with a pharmaceutically acceptable carrier.

* * * * *

SEQUENCE LISTING

<160> NUMBER OF SEQ ID NOS: 8

<210> SEQ ID NO 1
<211> LENGTH: 510
<212> TYPE: PRT
<213> ORGANISM: Homo sapiens

<400> SEQUENCE: 1

```
Met Glu Asp Thr Lys Glu Ser Asn Val Lys Thr Phe Cys Ser Lys Asn
 1               5                  10                  15

Ile Leu Ala Ile Leu Gly Phe Ser Ile Ile Ala Val Ile Ala Leu
                20                  25                  30

Leu Ala Val Gly Leu Thr Gln Asn Lys Ala Leu Pro Glu Asn Val Lys
                35                  40                  45

Tyr Gly Ile Val Leu Asp Ala Gly Ser Ser His Thr Ser Leu Tyr Ile
            50                  55                  60

Tyr Lys Trp Pro Ala Glu Lys Glu Asn Asp Thr Gly Val Val His Gln
 65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
                100                 105                 110

Arg Glu Val Ile Pro Arg Ser Gln His Gln Glu Thr Pro Val Tyr Leu
            115                 120                 125

Gly Ala Thr Ala Gly Met Arg Leu Leu Arg Met Glu Ser Glu Glu Leu
        130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
        290                 295                 300
```

-continued

```
Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510

<210> SEQ ID NO 2
<211> LENGTH: 1818
<212> TYPE: PRT
<213> ORGANISM: Homo sapiens

<400> SEQUENCE: 2

Ala Cys Cys Ala Cys Ala Cys Cys Ala Ala Gly Cys Ala Gly Cys Gly
1               5                   10                  15

Gly Cys Thr Gly Gly Gly Gly Gly Gly Gly Gly Ala Ala Ala Gly
            20                  25                  30

Ala Cys Gly Ala Gly Gly Ala Ala Gly Ala Gly Gly Ala Gly Gly
        35                  40                  45

Ala Ala Ala Ala Cys Ala Ala Ala Ala Gly Cys Thr Gly Cys Thr Ala
    50                  55                  60

Cys Thr Thr Ala Thr Gly Gly Ala Ala Gly Ala Thr Ala Cys Ala Ala
65                  70                  75                  80

Ala Gly Gly Ala Gly Thr Cys Thr Ala Ala Cys Gly Thr Gly Ala Ala
                85                  90                  95

Gly Ala Cys Ala Thr Thr Thr Gly Cys Thr Cys Cys Ala Ala Gly
            100                 105                 110

Ala Ala Thr Ala Thr Cys Cys Thr Ala Gly Cys Ala Thr Cys Cys
        115                 120                 125

Thr Thr Gly Gly Cys Thr Thr Cys Thr Cys Cys Thr Cys Ala Thr
    130                 135                 140

Cys Ala Thr Ala Gly Cys Thr Gly Thr Gly Ala Thr Ala Gly Cys Thr
145                 150                 155                 160

Thr Thr Gly Cys Thr Thr Gly Cys Thr Gly Thr Gly Gly Gly Gly Thr
                165                 170                 175
```

-continued

```
Thr Gly Ala Cys Cys Cys Ala Gly Ala Ala Cys Ala Ala Ala Gly Cys
            180                 185                 190

Ala Thr Thr Gly Cys Cys Ala Gly Ala Ala Ala Ala Cys Gly Thr Thr
        195                 200                 205

Ala Ala Gly Thr Ala Thr Gly Gly Gly Ala Thr Thr Gly Thr Gly Cys
    210                 215                 220

Thr Gly Gly Ala Thr Gly Cys Gly Gly Gly Thr Thr Cys Thr Thr Cys
225                 230                 235                 240

Thr Cys Ala Cys Ala Cys Ala Ala Gly Thr Thr Thr Ala Thr Ala Cys
                245                 250                 255

Ala Thr Cys Thr Ala Thr Ala Ala Gly Thr Gly Gly Cys Cys Ala Gly
            260                 265                 270

Cys Ala Gly Ala Ala Ala Ala Gly Gly Ala Gly Ala Ala Thr Gly Ala
        275                 280                 285

Cys Ala Cys Ala Gly Gly Cys Gly Thr Gly Gly Thr Gly Cys Ala Thr
    290                 295                 300

Cys Ala Ala Gly Thr Ala Gly Ala Ala Gly Ala Ala Thr Gly Cys Ala
305                 310                 315                 320

Gly Gly Gly Thr Thr Ala Ala Ala Gly Gly Thr Cys Cys Thr Gly Gly
                325                 330                 335

Ala Ala Thr Cys Thr Cys Ala Ala Ala Ala Thr Thr Thr Gly Thr Thr
            340                 345                 350

Cys Ala Gly Ala Ala Ala Gly Thr Ala Ala Ala Thr Gly Ala Ala Ala
        355                 360                 365

Thr Ala Gly Gly Cys Ala Thr Thr Thr Ala Cys Cys Thr Gly Ala Cys
    370                 375                 380

Thr Gly Ala Thr Thr Gly Cys Ala Thr Gly Gly Ala Ala Ala Gly Ala
385                 390                 395                 400

Gly Cys Thr Ala Gly Gly Gly Ala Ala Gly Thr Gly Ala Thr Thr Cys
                405                 410                 415

Cys Ala Ala Gly Gly Thr Cys Cys Cys Ala Gly Cys Ala Cys Cys Ala
            420                 425                 430

Ala Gly Ala Gly Ala Cys Ala Cys Cys Cys Gly Thr Thr Thr Ala Cys
        435                 440                 445

Cys Thr Gly Gly Gly Ala Gly Cys Cys Ala Cys Gly Gly Cys Ala Gly
    450                 455                 460

Gly Cys Ala Thr Gly Cys Gly Gly Thr Thr Gly Cys Thr Cys Ala Gly
465                 470                 475                 480

Gly Ala Thr Gly Gly Ala Ala Ala Gly Thr Gly Ala Ala Gly Ala Gly
                485                 490                 495

Thr Thr Gly Gly Cys Ala Gly Ala Cys Ala Gly Gly Gly Thr Thr Cys
            500                 505                 510

Thr Gly Gly Ala Thr Gly Thr Gly Gly Thr Gly Gly Ala Gly Ala Gly
        515                 520                 525

Gly Ala Gly Cys Cys Thr Cys Ala Gly Cys Ala Ala Cys Thr Ala Cys
    530                 535                 540

Cys Cys Cys Thr Thr Thr Gly Ala Cys Thr Thr Cys Cys Ala Gly Gly
545                 550                 555                 560

Gly Thr Gly Cys Cys Ala Gly Gly Ala Thr Cys Ala Thr Thr Ala Cys
                565                 570                 575

Thr Gly Gly Cys Cys Ala Ala Gly Ala Gly Gly Ala Ala Gly Gly Thr
            580                 585                 590
```

-continued

Gly Cys Cys Thr Ala Thr Gly Gly Cys Thr Gly Gly Ala Thr Thr Ala
595 600 605

Cys Thr Ala Thr Cys Ala Ala Cys Thr Ala Thr Cys Thr Gly Cys Thr
610 615 620

Gly Gly Gly Cys Ala Ala Ala Thr Thr Cys Ala Gly Thr Cys Ala Gly
625 630 635 640

Ala Ala Ala Ala Cys Ala Ala Gly Gly Thr Gly Gly Thr Thr Cys Ala
645 650 655

Gly Cys Ala Thr Ala Gly Thr Cys Cys Cys Ala Thr Ala Thr Gly Ala
660 665 670

Ala Ala Cys Cys Ala Ala Thr Ala Ala Thr Cys Ala Gly Gly Ala Ala
675 680 685

Ala Cys Cys Thr Thr Thr Gly Gly Ala Gly Cys Thr Thr Thr Gly Gly
690 695 700

Ala Cys Cys Thr Thr Gly Gly Gly Gly Gly Ala Gly Cys Cys Thr Cys
705 710 715 720

Thr Ala Cys Ala Cys Ala Ala Gly Thr Cys Ala Cys Thr Thr Thr Thr
725 730 735

Gly Thr Ala Cys Cys Cys Cys Ala Ala Ala Ala Cys Cys Ala Gly Ala
740 745 750

Cys Thr Ala Thr Cys Gly Ala Gly Thr Cys Cys Cys Cys Ala Gly Ala
755 760 765

Thr Ala Ala Thr Gly Cys Thr Cys Thr Gly Cys Ala Ala Thr Thr Thr
770 775 780

Cys Gly Cys Cys Thr Cys Thr Ala Thr Gly Gly Cys Ala Ala Gly Gly
785 790 795 800

Ala Cys Thr Ala Cys Ala Ala Thr Gly Thr Cys Thr Ala Cys Ala Cys
805 810 815

Ala Cys Ala Thr Ala Gly Cys Thr Thr Cys Thr Thr Gly Thr Gly Cys
820 825 830

Thr Ala Thr Gly Gly Gly Ala Ala Gly Gly Ala Thr Cys Ala Gly Gly
835 840 845

Cys Ala Cys Thr Cys Thr Gly Gly Cys Ala Gly Ala Ala Ala Cys Thr
850 855 860

Gly Gly Cys Cys Ala Ala Gly Gly Ala Cys Ala Thr Thr Cys Ala Gly
865 870 875 880

Gly Thr Thr Gly Cys Ala Ala Gly Thr Ala Ala Thr Gly Ala Ala Ala
885 890 895

Thr Thr Cys Thr Cys Ala Gly Gly Gly Ala Cys Cys Cys Ala Thr Gly
900 905 910

Cys Thr Thr Thr Cys Ala Thr Cys Cys Thr Gly Gly Ala Thr Ala Thr
915 920 925

Ala Ala Gly Ala Ala Gly Gly Thr Ala Gly Thr Gly Ala Ala Cys Gly
930 935 940

Thr Ala Ala Gly Thr Gly Ala Cys Cys Thr Thr Thr Ala Cys Ala Ala
945 950 955 960

Gly Ala Cys Cys Cys Cys Cys Thr Gly Cys Ala Cys Cys Ala Ala Gly
965 970 975

Ala Gly Ala Thr Thr Thr Gly Ala Gly Ala Thr Gly Ala Cys Thr Cys
980 985 990

Thr Thr Cys Cys Ala Thr Thr Cys Cys Ala Gly Cys Ala Gly Thr Thr
995 1000 1005

Thr Gly Ala Ala Ala Thr Cys Cys Ala Gly Gly Gly Thr Ala Thr Thr

-continued

```
                1010                1015                1020
Gly Gly Ala Ala Ala Cys Thr Ala Thr Cys Ala Ala Cys Ala Ala Thr
1025                1030                1035                1040
Gly Cys Cys Ala Thr Cys Ala Ala Ala Gly Cys Ala Thr Cys Cys Thr
                1045                1050                1055
Gly Gly Ala Gly Cys Thr Cys Thr Thr Cys Ala Ala Cys Ala Cys Cys
            1060                1065                1070
Ala Gly Thr Thr Ala Cys Thr Gly Cys Cys Thr Thr Ala Cys Thr
        1075                1080                1085
Cys Cys Cys Ala Gly Thr Gly Thr Gly Cys Cys Thr Thr Cys Ala Ala
    1090                1095                1100
Thr Gly Gly Ala Thr Thr Thr Thr Cys Thr Thr Gly Cys Cys Ala
1105                1110                1115                1120
Cys Cys Ala Cys Thr Cys Cys Ala Gly Gly Gly Gly Ala Thr Thr
                1125                1130                1135
Thr Thr Gly Gly Gly Gly Cys Ala Thr Thr Thr Cys Ala Gly Cys
            1140                1145                1150
Thr Thr Thr Thr Thr Ala Cys Thr Thr Thr Gly Thr Gly Ala Thr Gly
        1155                1160                1165
Ala Ala Gly Thr Thr Thr Thr Thr Ala Ala Ala Cys Thr Thr Gly Ala
    1170                1175                1180
Cys Ala Thr Cys Ala Gly Ala Gly Ala Ala Ala Gly Thr Cys Thr Cys
1185                1190                1195                1200
Thr Cys Ala Gly Gly Ala Ala Ala Gly Gly Thr Gly Ala Cys Thr
                1205                1210                1215
Gly Ala Gly Ala Thr Gly Ala Thr Gly Ala Ala Ala Ala Gly Thr
            1220                1225                1230
Thr Cys Thr Gly Thr Gly Cys Thr Cys Ala Gly Cys Cys Thr Thr Gly
        1235                1240                1245
Gly Gly Ala Gly Gly Ala Gly Ala Thr Ala Ala Ala Ala Cys Ala
    1250                1255                1260
Thr Cys Thr Thr Ala Cys Gly Cys Thr Gly Gly Ala Gly Thr Ala Ala
1265                1270                1275                1280
Ala Gly Gly Ala Gly Ala Ala Gly Thr Ala Cys Cys Thr Gly Ala Gly
            1285                1290                1295
Thr Gly Ala Ala Thr Ala Cys Thr Gly Cys Thr Thr Thr Cys Thr
        1300                1305                1310
Gly Gly Thr Ala Cys Cys Thr Ala Cys Ala Thr Thr Cys Thr Cys Thr
    1315                1320                1325
Cys Cys Cys Thr Cys Thr Thr Cys Thr Gly Cys Ala Ala Gly Gly
1330                1335                1340
Cys Thr Ala Thr Cys Ala Thr Thr Cys Ala Cys Ala Gly Cys Thr
1345                1350                1355                1360
Gly Ala Thr Thr Cys Thr Gly Gly Gly Ala Gly Cys Ala Cys Ala
                1365                1370                1375
Thr Cys Cys Ala Thr Thr Thr Cys Ala Thr Thr Gly Gly Cys Ala Ala
            1380                1385                1390
Gly Ala Thr Cys Cys Ala Gly Gly Gly Cys Ala Gly Cys Gly Ala Cys
        1395                1400                1405
Gly Cys Cys Gly Gly Cys Thr Gly Gly Ala Cys Thr Thr Gly Gly
    1410                1415                1420
Gly Cys Thr Ala Cys Ala Thr Gly Cys Thr Gly Ala Ala Cys Cys Thr
1425                1430                1435                1440
```

```
Gly Ala Cys Cys Ala Ala Cys Ala Thr Gly Ala Thr Cys Cys Ala
            1445                1450                1455
Gly Cys Thr Gly Ala Gly Cys Ala Ala Cys Cys Ala Thr Thr Gly Thr
            1460                1465                1470
Cys Cys Ala Cys Ala Cys Cys Thr Cys Thr Cys Thr Cys Cys Ala
            1475                1480                1485
Cys Thr Cys Cys Ala Cys Cys Thr Ala Thr Gly Thr Cys Thr Thr Cys
            1490                1495                1500
Cys Thr Cys Ala Thr Gly Gly Thr Thr Cys Thr Ala Thr Thr Cys Thr
1505                1510                1515                1520
Cys Cys Cys Thr Gly Gly Thr Cys Cys Thr Thr Thr Cys Ala Cys
            1525                1530                1535
Ala Gly Thr Gly Gly Cys Cys Ala Thr Cys Ala Thr Ala Gly Gly Cys
            1540                1545                1550
Thr Thr Gly Cys Thr Thr Ala Thr Cys Thr Thr Thr Cys Ala Cys Ala
            1555                1560                1565
Ala Gly Cys Cys Thr Thr Cys Ala Thr Ala Thr Thr Cys Thr Gly
            1570                1575                1580
Gly Ala Ala Ala Gly Ala Thr Ala Thr Gly Gly Thr Ala Thr Ala Gly
1585                1590                1595                1600
Cys Ala Ala Ala Ala Gly Cys Ala Gly Cys Thr Gly Ala Ala Ala Thr
            1605                1610                1615
Ala Thr Gly Cys Thr Gly Gly Cys Thr Gly Gly Ala Gly Thr Gly Ala
            1620                1625                1630
Gly Gly Ala Ala Ala Ala Ala Ala Thr Cys Gly Thr Cys Cys Ala Gly
            1635                1640                1645
Gly Gly Ala Gly Cys Ala Thr Thr Thr Cys Cys Thr Cys Cys Ala
            1650                1655                1660
Thr Cys Gly Cys Ala Gly Thr Gly Thr Thr Cys Ala Ala Gly Gly Cys
1665                1670                1675                1680
Cys Ala Thr Cys Cys Thr Thr Cys Cys Cys Thr Gly Thr Cys Thr Gly
            1685                1690                1695
Cys Cys Ala Gly Gly Gly Cys Cys Ala Gly Thr Cys Thr Thr Gly Ala
            1700                1705                1710
Cys Gly Ala Gly Thr Gly Thr Gly Ala Ala Gly Cys Thr Thr Cys Cys
            1715                1720                1725
Thr Thr Gly Gly Cys Thr Thr Thr Ala Cys Thr Gly Ala Ala Gly
            1730                1735                1740
Cys Cys Thr Thr Thr Cys Thr Thr Thr Gly Gly Ala Gly Gly Thr
1745                1750                1755                1760
Ala Thr Thr Cys Ala Ala Thr Ala Thr Cys Cys Thr Thr Thr Gly Cys
            1765                1770                1775
Cys Thr Cys Ala Ala Gly Gly Ala Cys Thr Thr Cys Gly Gly Cys Ala
            1780                1785                1790
Gly Ala Thr Ala Cys Thr Gly Thr Cys Thr Cys Thr Thr Thr Cys Ala
            1795                1800                1805
Thr Gly Ala Gly Thr Thr Thr Thr Thr Cys
    1810                1815

<210> SEQ ID NO 3
<211> LENGTH: 11
<212> TYPE: PRT
<213> ORGANISM: Bovine
```

-continued

```
<400> SEQUENCE: 3

Glu Thr Pro Val Tyr Leu Gly Ala Thr Ala Gly
 1               5                  10

<210> SEQ ID NO 4
<211> LENGTH: 5
<212> TYPE: PRT
<213> ORGANISM: Bovine

<400> SEQUENCE: 4

Leu Leu Arg Met Glu
 1               5

<210> SEQ ID NO 5
<211> LENGTH: 13
<212> TYPE: PRT
<213> ORGANISM: Bovine
<220> FEATURE:
<221> NAME/KEY: UNSURE
<222> LOCATION: (8)
<223> OTHER INFORMATION: Xaa, where Xaa = any amino acid

<400> SEQUENCE: 5

Ala Asp Lys Ile Leu Ala Asn Xaa Val Ala Ser Ser Ile
 1               5                  10

<210> SEQ ID NO 6
<211> LENGTH: 10
<212> TYPE: PRT
<213> ORGANISM: Bovine

<400> SEQUENCE: 6

Tyr Pro Phe Asp Phe Gln Gly Ala Arg Ile
 1               5                  10

<210> SEQ ID NO 7
<211> LENGTH: 19
<212> TYPE: PRT
<213> ORGANISM: Porcine

<400> SEQUENCE: 7

Lys Ser Asp Thr Gln Glu Thr Tyr Gly Ala Leu Asp Leu Gly Gly Ala
 1               5                  10                  15

Ser Thr Gln

<210> SEQ ID NO 8
<211> LENGTH: 16
<212> TYPE: PRT
<213> ORGANISM: Human and bovine

<400> SEQUENCE: 8

Lys Ser Asp Thr Gln Glu Thr Tyr Gly Ala Leu Asp Leu Gly Gly Ala
 1               5                  10                  15
```